(12) United States Patent
Couves et al.

(10) Patent No.: US 11,493,488 B2
(45) Date of Patent: Nov. 8, 2022

(54) QUANTITATIVE METHOD FOR DETERMINING THE ORGANIC ACID CONTENT OF CRUDE OIL

(71) Applicant: BP Exploration Operating Company Limited, Middlesex (GB)

(72) Inventors: John William Couves, Bourne End (GB); Christianne Clare Wicking, Reading (GB)

(73) Assignee: BP EXPLORATION OPERATING COMPANY LIMITED, Middlesex (GB)

( * ) Notice: Subject to any disclaimer, the term of this patent is extended or adjusted under 35 U.S.C. 154(b) by 440 days.

(21) Appl. No.: 16/638,129

(22) PCT Filed: Aug. 16, 2018

(86) PCT No.: PCT/EP2018/072276
§ 371 (c)(1),
(2) Date: Feb. 10, 2020

(87) PCT Pub. No.: WO2019/034756
PCT Pub. Date: Feb. 21, 2019

(65) Prior Publication Data
US 2020/0240963 A1 Jul. 30, 2020

(30) Foreign Application Priority Data
Aug. 17, 2017 (EP) ..................... 17186718

(51) Int. Cl.
*G01N 30/72* (2006.01)
*G01N 33/28* (2006.01)
(Continued)

(52) U.S. Cl.
CPC ............. *G01N 30/724* (2013.01); *G01N 1/38* (2013.01); *G01N 30/482* (2013.01);
(Continued)

(58) Field of Classification Search
None
See application file for complete search history.

(56) References Cited

U.S. PATENT DOCUMENTS 6,464,859 B1  10/2002  Duncum et al.
8,812,271 B1   8/2014  Brady et al.
(Continued)

FOREIGN PATENT DOCUMENTS

CN        1334857 A      2/2002

OTHER PUBLICATIONS

PCT/EP2018/072276 International Search Report and Written Opinion dated Sep. 14, 2018 (18 p.).
(Continued)

*Primary Examiner* — Daniel S Larkin
(74) *Attorney, Agent, or Firm* — Conley Rose, P.C.

(57) ABSTRACT

A method for analysing a crude oil to determine the amount of organic acid compounds contained in the crude oil includes extracting the organic acid compounds from a sample of crude oil to form an extract and determining the amount of the extracted organic acids In addition, the method includes dissolving the extract in a polar solvent to form a solution of the extracted organic acid compounds Further, the method includes introducing a sample of the solution of the extracted organic acid to an apparatus including a reversed phase liquid chromatography (LC) column and a mass spectrometer (MS) arranged in series. The reversed phase LC column contains a hydrophobic sorbent and the mobile phase for the LC column includes a polar organic solvent. Still further, the method includes separating the organic acid compounds in the LC column of the LC-MS apparatus and continuously passing the separated organic acid compounds from the LC column to the MS of the LC-MS apparatus to ionize the organic acid compounds and
(Continued)

to obtain a chromatogram with mass spectral data over time for the ionized organic acid compounds. Moreover, the method includes determining the area(s) under the peak(s) in an extracted ion chromatogram derived from the mass spectral data assigned to one or more organic acid compounds. The method also includes determining the amount of the organic acid compound(s) in the sample by comparing the area under the peak(s) assigned to the organic acid compound(s) with the area under a peak in an extracted ion chromatogram assigned to a specific amount of a standard organic acid compound. In addition, the method includes extrapolating from the amount of the organic acid compound(s) in the sample to provide the total amount of the organic acid compound(s) in the extract.

16 Claims, 5 Drawing Sheets

(51) Int. Cl.
  *G01N 1/38*   (2006.01)
  *B01J 20/281*   (2006.01)
  *G01N 30/86*   (2006.01)
  *G01N 30/00*   (2006.01)

(52) U.S. Cl.
  CPC ..... *G01N 30/8679* (2013.01); *G01N 33/2876* (2013.01); *G01N 2030/484* (2013.01)

(56) References Cited

U.S. PATENT DOCUMENTS

| | | |
|---|---|---|
| 2002/0086434 A1 | 7/2002 | Roussis et al. |
| 2015/0219615 A1 | 8/2015 | Nyadong et al. |
| 2015/0300149 A1 | 10/2015 | Collins et al. |
| 2017/0108474 A1 | 4/2017 | Kondo et al. |

OTHER PUBLICATIONS

Flego, Cristina et al., "Evolution of Naphthenic Acids During the Corrosion Process," America Chemical Society, Energy Fuels, 2014, vol. 28, No. 3, pp. 1701-1708 (8 p.).

Jones, D.M. et al., "Determination of Naphthenic Acids in Crude Olis Using Nonaqueous Ion Exchange Solid-Phase Extraction," America Chemical Society, Analytical Chemistry, vol. 73, No. 3, Feb. 1, 2001, pp. 703-707 (5 p.).

Mapolelo, Mmilili M. et al., "Characterization of Naphthenic Acids in Crude Oils and Naphthenates by Electrospray Ionization FT-ICR Mass Spectrometry," International Journal of Mass Spectrometry, vol. 300, No. 2, 2011, pp. 149-157 (p.).

Mediaas, Heidi et al,. "The Acid-IER Method-a Method for Selective Isolation of Carboxylic Acids form Crude Oils and Other Organic Solvents," Society of Petroleum Engineers, Aberdeen, UK Jan. 29-30, 2003 (SPE 80404) (7 p.).

Oian, Kuangnan et al., "Resolution and Identification of Elemental Compositions for More than 300 Crude Acids in Heavy Petroleum by Negative-Ion Microelectrospray High-Field Fourier Transform Ion Cyclotron Resonance Mass Spectrometry," America Chemical Society, Energy Fuels, 2001, vol. 15, pp. 1505-1511 (7 p.).

Wan, Yi et al., "Naphthenic Acids in Coastal Sediments after the Hebei Spirit Oil Spill: A Potential Indicator for Oil Contamination," Environmental Science & Technology, vol. 48, No. 7, Feb. 28, 2014, pp. 4153-4162 (10 p.).

Smith, B.E. et al., "A Derivatisation and Liquid Chromatography/ Electrospray Ionisation Multistage Mass Spectrometry Method for the Characterisation of Naphthenic Acids," Rapid Communications in Mass Spectrometry, vol. 22, pp. 3909-3927, Sep. 29, 2008 (19 p.).

Chinese Office Action dated Aug. 1, 2022, for Chinese Application No. 201880067986.0 (15 p.).

English Translation of Chinese Office Action dated Aug. 1, 2022, for Chinese Application No. 201880067986.0 (12 p.).

QUANTITATIVE METHOD FOR DETERMINING THE ORGANIC ACID CONTENT OF CRUDE OIL

CROSS-REFERENCE TO RELATED APPLICATIONS

This application is a 35 U.S.C. § 371 national stage application of PCT/EP2018/072276 filed Aug. 16, 2018, entitled "Quantitative Method for Determining the Organic Acid Content of Crude Oil," which claims priority to European Application No. 17186718.7 filed Aug. 17, 2017, and entitled "Quantitative Method for Determining the Organic Acid Content of Crude Oil," each of which is hereby incorporated herein by reference in its entirety for all purposes.

STATEMENT REGARDING FEDERALLY SPONSORED RESEARCH OR DEVELOPMENT

Not applicable.

BACKGROUND

The present invention relates to a quantitative method for determining the amount of organic acid compounds in crude oil.

The total acid number (TAN) for a crude oil is a measurement of acidity and is determined by the amount of potassium hydroxide in milligrams that is needed to neutralize the acids in one gram of oil. Although the TAN value provides an indication of the acidity of a crude oil, the measurement provides no information concerning the types of organic acid compounds (typically, carboxylic acid compounds) in the crude oil.

It would therefore be advantageous to find a method that quantifies the types or classes of organic acid compounds in samples of different crude oils to provide a chemical signature for the crude oil. Thus, the amounts of types or classes of organic acid compounds in crude oils produced from different reservoirs may vary. It is also believed that the amounts of types or classes of organic acid compounds in a crude oil produced from a reservoir may vary over time. Further, the amounts of types or classes of organic acid compounds in a crude oil may vary when an enhanced oil recovery (EOR) method, for example, low salinity waterflooding, is used for recovery of crude oil from the reservoir. Accordingly, a change in the amount of different types or classes of organic acid compounds in the crude oil produced from a reservoir may provide an indication of the effectiveness of an EOR method.

SUMMARY

According to a first aspect of the present invention, there is provided a method for analyzing a crude oil to determine the amount of at least one organic acid compound contained in the crude oil comprising:
extracting the organic acid compounds from a sample of a known amount of the crude oil to form an extract comprising the organic acid compounds and determining the amount of the extracted organic acid compounds;
dissolving the extract in a specific volume of at least one polar solvent to form a solution of the extracted organic acid compounds in the polar solvent(s);
introducing a sample comprising a specific volume of the solution of the extracted organic acid compounds to an apparatus comprising a reversed phase liquid chromatography (LC) column and a mass spectrometer (MS) arranged in series (hereinafter LC-MS apparatus) wherein the reversed phase LC column contains a hydrophobic sorbent and the mobile phase for the LC column comprises a polar organic solvent;
separating the organic acid compounds in the LC column of the LC-MS apparatus and continuously passing the separated organic acid compounds removed from the LC column to the MS of the LC-MS apparatus to ionize the organic acid compounds and to obtain a chromatogram with mass spectral data over time for the ionized organic acid compounds;
determining the area under at least one peak in an extracted ion chromatogram, extracted from the mass spectral data, assigned to at least one organic acid compound; determining the amount of the organic acid compound in the sample of the solution of the extracted organic acids by comparing the area under the peak(s) assigned to the organic acid compound(s) with the area under a peak in an extracted ion chromatogram assigned to a specific amount of a standard organic acid compound; and extrapolating from the amount of the organic acid compound in the sample of the solution of the extracted organic acids to provide the total amount of the organic acid compound in the extract.

Further features and advantages of the invention will become apparent from the following description of preferred embodiments of the invention, given by way of example only, which is made with reference to the accompanying drawings.

DEFINITIONS

Figure 1:
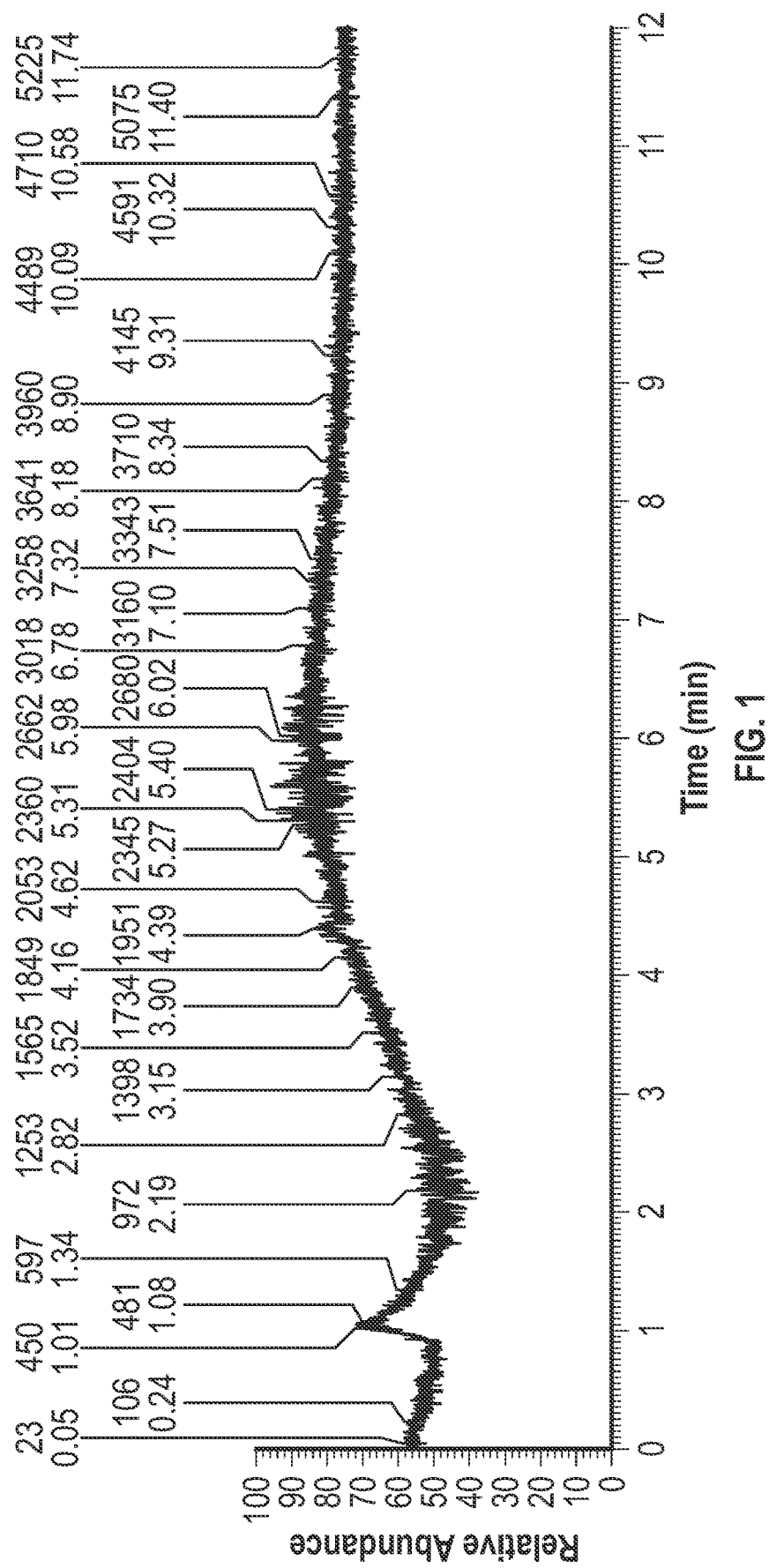
FIG. 1 is a chromatogram for a solution of organic acid compounds extracted from a sample of crude oil showing the relative abundance (intensities) of ionised organic acid compounds (mass spectral data) over time.
Figure 2:
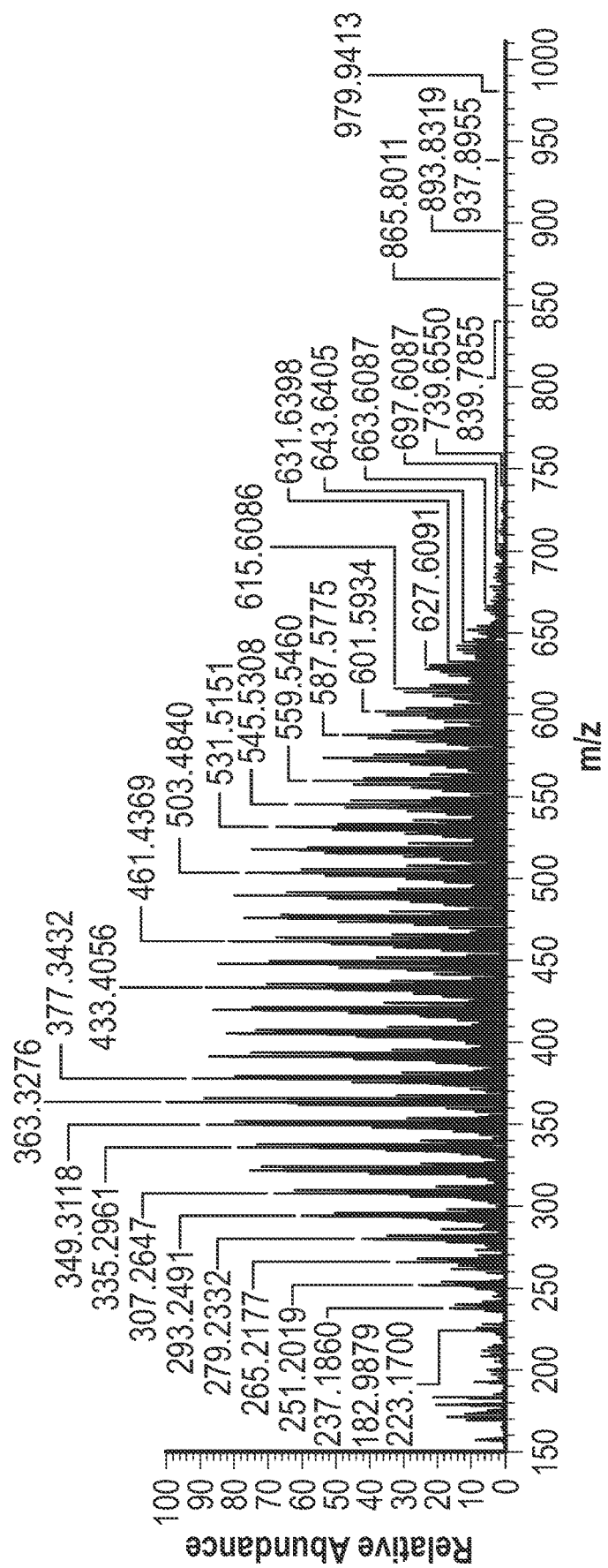
FIG. 2 is generated from FIG. 1 and is a mass spectrum showing the relative abundance of all ions having m/z values (where m is mass and z is charge) in the range of 150 to 1100 during the period over which organic acid compounds were eluted from the LC column of the LC-MS apparatus.
Figure 3:
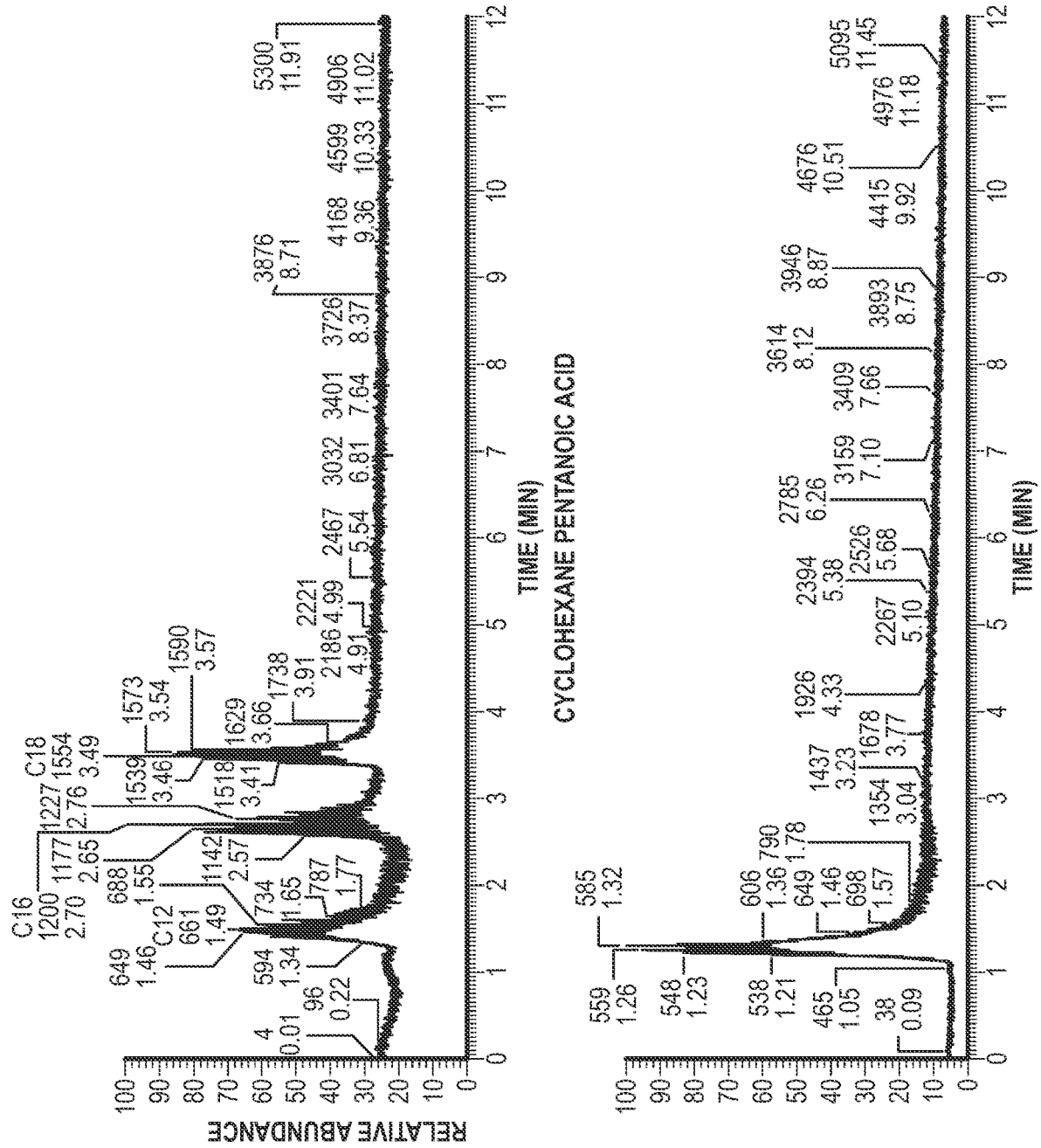
FIG. 3 shows an extracted ion chromatogram (EIC) for a solution of three standard carboxylic acids (dodecanoic acid, hexadecanoic acid and octadecanoic acid) in methanol and an EIC for a solution of a further standard carboxylic acid (cyclohexylpentanoic acid) in methanol. Dodecanoic acid, hexadecanoic acid and octadecanoic acid each have a Double Bond Equivalent (DBE) value of 1 while cyclopentanoic acid has a DBE value of 2 (DBE is defined below).
Figure 4:
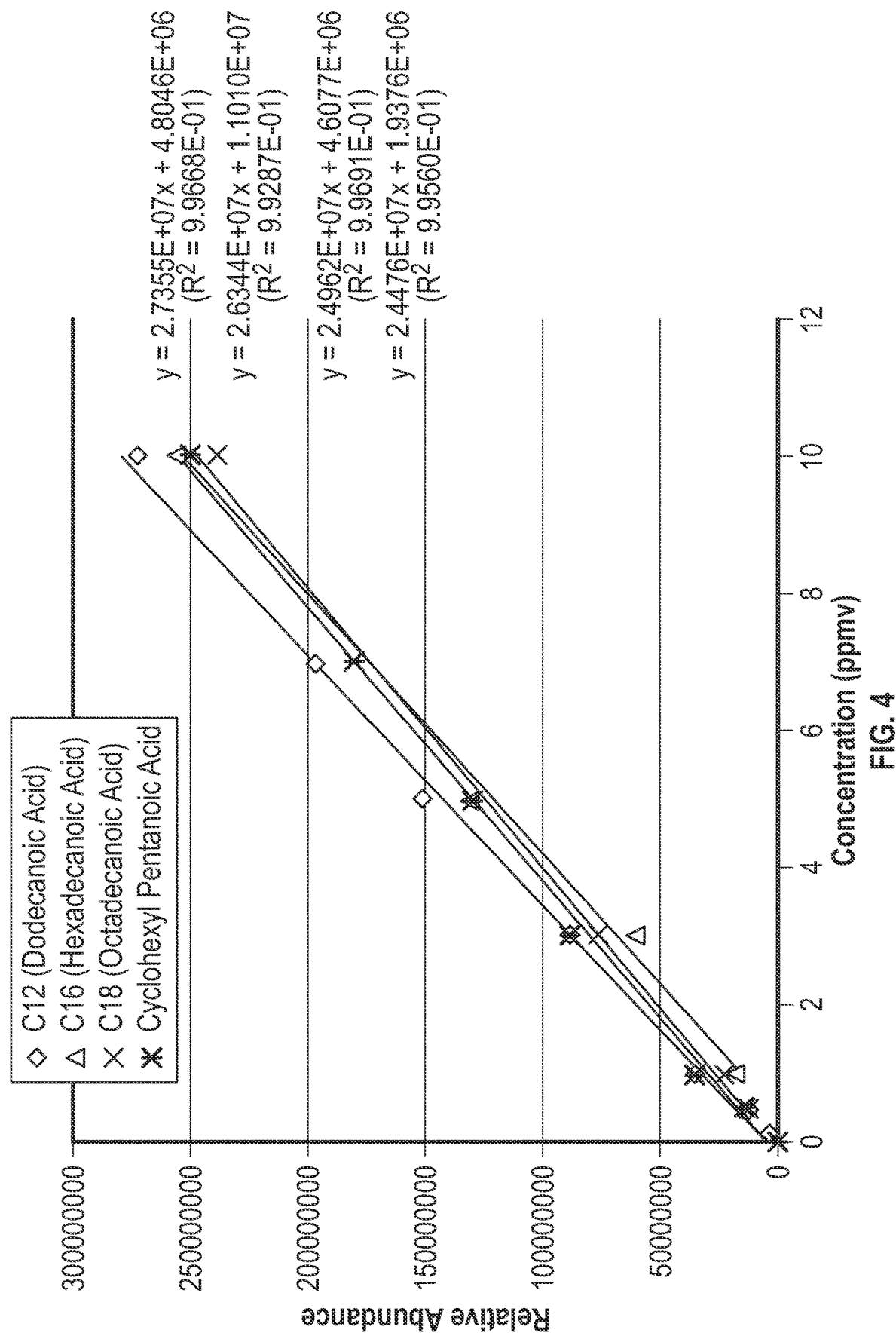
FIG. 4 shows plots (calibration curves) of the relative abundance (areas under the peaks in the extracted ion chromatograms of FIG. 3) against concentration in parts per million (ppm) for the four standard carboxylic acids (dodecanoic acid, hexadecanoic acid, octadecanoic acid and cyclohexylpentanoic acid).
Figure 5:
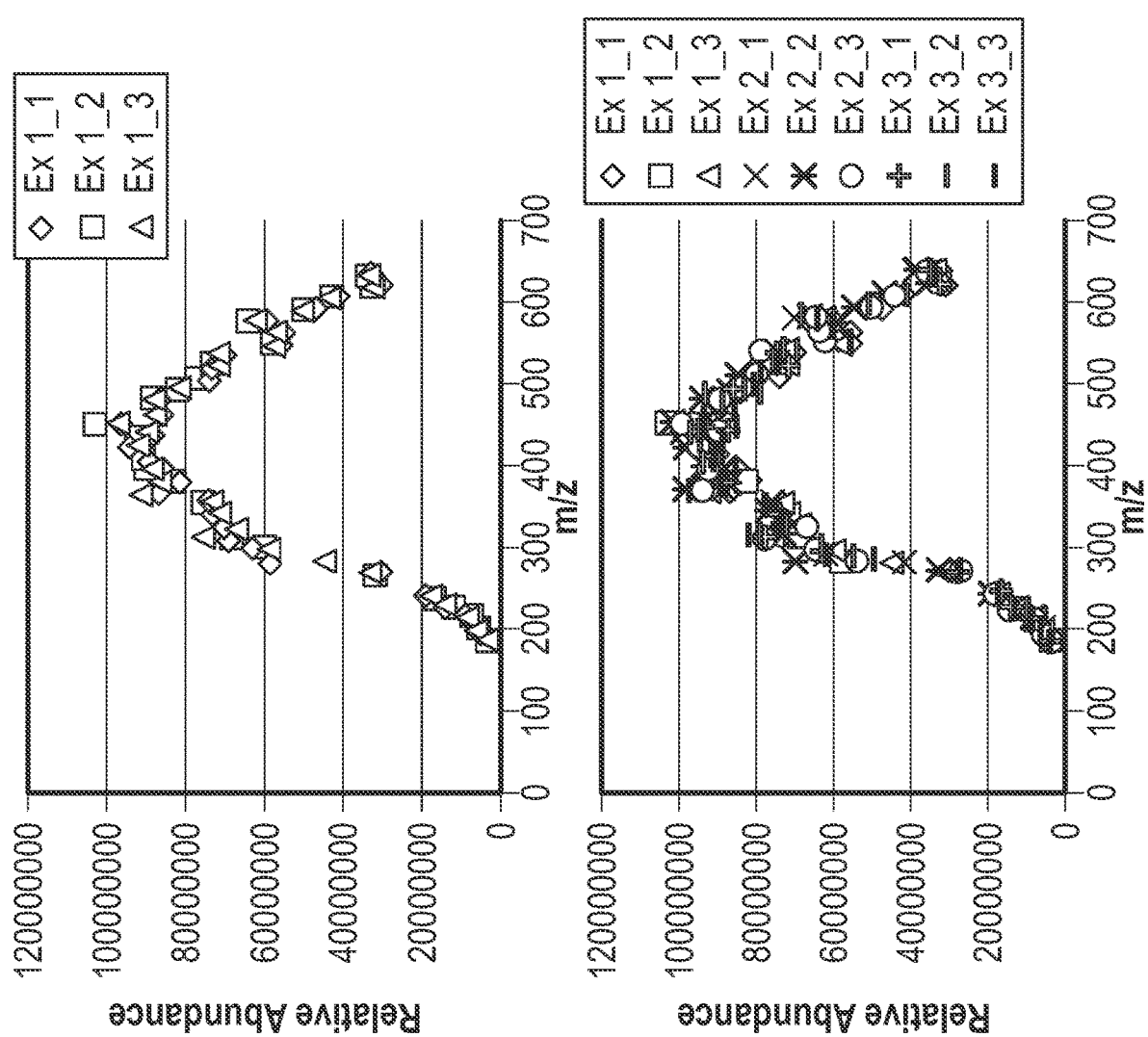
FIG. 5 shows the areas under the peaks for individual organic acid compounds in the series of compounds having DBE values of 1 across an m/z range of 0 to 800. Three samples of the crude oil were extracted to give three different extracts while liquid chromatography-mass spectrometry analysis of solutions of each of the extracts was repeated in triplicate. The results presented in FIG. 5 show good repeatability of the method of the present invention.

Throughout the following description the following terms are referred to:

"Organic acid compounds" are compounds contained in the sample of crude oil that are Bronsted acids (hydrogen donors) including carboxylic acids (in particular, fatty acids and naphthenic acids) and organic sulfonic acids.

"Ionized organic acid compounds" are organic acid compounds that have been ionized in the mass spectrometer of the LC-MS apparatus with minimal fragmentation of the ionized compounds.

"Extract" comprises the organic acid compounds that are selectively separated from a sample of crude oil.

A "chromatogram" is a representation of mass spectrometry data as a chromatogram where the x-axis represents time and the y-axis represents total ion intensity. This data representation may be used for mass spectrometry data obtained using a liquid-chromatography-mass spectrometer (LC-MS) apparatus. Liquid chromatography separates mixtures of organic molecules while mass spectrometry provides formulae assignment for the individual organic molecules. Accordingly, the x-axis represents retention time on the LC column of the LC-MS apparatus. In an "extracted ion chromatogram (EIC)", one or more m/z values representing one or more molecules of interest are extracted from the entire data set of a chromatogram.

Double Bond Equivalent (DBE) is a way of expressing the degree of unsaturation of an organic compound and is discussed in more detail below.

"Standard solution" of a carboxylic acid is a solution containing a precisely known concentration of a standard carboxylic acid of known chemical composition formed by dissolving a known mass of the carboxylic acid in a specific volume of a polar solvent.

"Standard carboxylic acid" is a carboxylic acid of known chemical composition used to prepare a "standard solution".

"Recovery factor acid" is an organic acid, typically, a carboxylic acid, that is added to the sample of oil in a known amount to determine the yield (also known as recovery) of acids in the extraction step of the method of the present invention.

"Recovery of acids" is the ratio of the amount of recovery factor acid in the extract to the amount of recovery factor acid added to the sample of oil.

"M/Z" is the mass (m) to charge (z) ratio for the ionised compounds recorded in a spectrum.

"High Resolution Mass Spectrometry (HRMS)" is a mass spectrometric analytical technique that produces spectra of the mass-to-charge (m/z) values of ionisable compounds to an accuracy of four decimal places.

"Liquid chromatography-mass spectrometry" means a mass spectrometry technique using an apparatus comprising a liquid chromatography (LC) column arranged upstream of a mass spectrometer (MS) and wherein the LC column separates the components of a sample based on a parameter (e.g. polarity or size) prior to introducing the separated components of the sample into the MS.

DETAILED DESCRIPTION

The method of the present invention involves determining the amount of one or more individual organic acid compounds in an extract that is extracted from a sample of crude oil. Thus, samples of crude oil taken from different reservoirs contain different amounts or types of organic acid compounds such as carboxylic acid compounds. Further, the amounts or types of organic acid compounds, in particular, carboxylic acids in the crude oil produced from a reservoir may vary depending on the recovery method for the reservoir, for example, may vary following implementation of an enhanced oil recovery (EOR) method such as low salinity waterflooding.

Preferably, the organic acid compounds are selectively extracted from a sample of a known amount of the crude oil to form an extract comprising the organic acid compounds by:

(i) diluting a sample comprised of a known amount of the crude oil with an organic solvent;
(ii) passing the diluted crude oil sample through an adsorbent column or cartridge comprising a particulate weakly basic sorbent (solid phase sorbent) to adsorb organic acid compounds from the diluted crude oil sample;
(iii) passing an eluent comprising at least one volatile polar organic solvent having a boiling point lower than the boiling points of the organic acid compounds through the column or cartridge to elute the adsorbed organic acid compounds from the sorbent and removing from the column or cartridge an effluent comprising a solution of the organic acid compounds in the volatile polar organic solvent; and
(iv) separating an extract comprising the organic acid compounds from the eluent by evaporation of the volatile polar organic solvent(s) and determining the amount of the extract.

The dilution step (i) may be omitted if the crude oil is a light (low viscosity) oil.

Typically, the known amount of crude oil is a known weight (or mass) of crude oil.

The minimum weight of a sample of crude oil (for a quantitative measurement of the content of a specific organic acid compound or of a specific class of homologous organic acid compounds) is dependent upon the content of organic acid compounds in the crude oil with the minimum weight decreasing with increasing content of organic acid compounds. As discussed above, TAN value may be used as an indication of the content of the organic acid compounds in a crude oil. Accordingly, the minimum weight of a sample of crude oil decreases with increasing TAN value of the crude oil. Typically, the minimum weight of the sample of crude oil is in the range 0.1 to 1 grams (g) with the minimum amount decreasing with increasing TAN value of the crude oil. Typically, the crude oil sample has a weight in the range of 0.5 to 5 g, preferably 0.5 to 2 g, for example, 1 to 2 g, although larger sized samples of crude oil may also be used.

The sample of crude oil is preferably diluted with an organic solvent selected from aliphatic organic solvents, aromatic organic solvents such as toluene or xylene, tetrahydrofuran, diethyl ether and halogenated aliphatic organic solvents. Typically, the volumetric ratio of organic solvent to crude oil in the diluted crude oil sample is in the range of 1:1 to 10:1, preferably, 1:1 to 3:1.

The organic acid compounds are then extracted from the diluted crude oil samples using solid phase extraction (SPE) by passing the diluted crude oil samples through a column or cartridge comprising a solid phase sorbent that selectively adsorbs the organic acid compounds from the diluted crude oil sample. The solid phase sorbent preferably comprises a weakly basic sorbent. Preferably, the solid phase sorbent comprises silica particles that have been functionalized with an amine containing group such as an $-O-Si(CH_3)_2(CH_2)_n-NH_2$ group wherein n is an integer from 1 to 10, preferably, 2 to 8, more preferably, 2 to 5, in particular, 3.

SPE cartridges comprising an amine functionalised silica sorbent include Mega BE-NH2 manufactured by Agilent Technologies having a tube size of 6 mL and a sorbent weight of 1 g. Alternatively, the solid phase sorbent may comprise silica particles that have been functionalised with a quaternary amine group. A suitable SPE cartridge comprising a quaternary amine functionalised silica sorbent is a SAX quaternary amine ion exchange cartridge manufactured by International Sorbent Technology having a sorbent weight of 10 g. The size of the column or cartridge is dependent on the weight of the crude oil sample, its content of organic acid compounds and on the adsorption capacity of column or cartridge. Accordingly, larger or smaller columns or cartridges may also be used. Typically, larger columns or cartridges are used for larger samples of crude oil, especially, when the crude oil has a high TAN value. This is because the adsorbent capacity of the column or cartridge should be sufficient to adsorb all of the organic acid compounds contained in the crude oil sample.

The organic acid compounds are then eluted from the sorbent using an eluent comprising a mixture of volatile polar organic solvents having boiling points below the boiling points of the adsorbed organic acid compounds. Preferably, the eluent comprises a major portion of a first polar solvent selected from a $C_1$ to $C_3$ alcohol, tetrahydrofuran and diethyl ether in particular, methanol or diethyl ether and a minor portion of a $C_1$ to $C_3$ carboxylic acid solvent, in particular, formic acid or acetic acid. Typically, the carboxylic acid solvent is present in the eluent in an amount of up to 15% by volume, preferably in an amount in the range of from 1.5 to 10% by volume, preferably, more preferably from 2 to 7.5% by volume, in particular, from 2 to 5% by volume.

The effluent removed from the column or cartridge is collected and the eluent comprising the mixture of volatile polar organic solvents is removed, for example, by evaporation to give an extract comprising the organic acid compounds. The mass of the extract may then be determined. Typically, the effluent from the sorbent column is collected in a vessel of known mass and the vessel is re-weighed following complete evaporation of the volatile polar organic solvent (leaving the extract comprising the organic acid compounds). The difference in the mass of the vessel following evaporation of the volatile polar organic solvent and the mass of the vessel is the mass of the extract.

Typically, the organic acid compounds that are contained in the extract include linear aliphatic carboxylic acids, branched aliphatic carboxylic acids, monocyclic naphthenic acids, bicyclic naphthenic acids, polynuclear naphthenic acids, aromatic acids, binuclear aromatic acids, and polynuclear aromatic acids. The extract may then be dissolved in a specific volume of at least one polar organic solvent to form a solution of the extract (i.e., a solution of the extracted organic acid compounds) in the polar organic solvent(s). Preferably, the polar organic solvent is selected from halogenated organic solvents, alcohol solvents and mixtures thereof. Preferably, the extract is first dissolved in a specific volume of a halogenated organic solvent and the resulting solution is then diluted with a specific volume of an alcohol solvent to provide a solution of the extracted organic acid compounds in a mixture of the halogenated organic solvent and alcohol solvent. Typically, the volumetric ratio of the halogenated organic solvent to the alcohol solvent in the solution of the extracted organic acid compounds is from about 1:1 to about 1:2. The halogenated organic solvent is preferably, a chlorinated organic solvent, in particular, dichloromethane. The alcohol solvent is preferably a $C_1$ to $C_3$ alcohol, in particular, methanol or ethanol, preferably, methanol.

The solutions of the extract (containing the organic acid compounds) are then analysed using a reversed phase liquid chromatography-mass spectrometry method that uses a high resolution mass spectrometer (HRMS) as the detector. Thus, a specific volume of the solution of the extracted organic acid compounds is injected into the mobile phase that is continuously passed through the liquid chromatography (LC) column of the LC-MS apparatus.

Suitably, the LC column of the LC-MS apparatus comprises a solid phase sorbent (stationary phase) that separates the organic acid compounds based on polarity by differential partitioning between the liquid mobile phase and stationary phase. The liquid chromatography step of the method of the present invention may employ reversed phase liquid chromatography in which the stationary phase is hydrophobic (less polar) than the mobile phase. Preferably, the stationary phase comprises alkylsilyl-modified silica particles wherein the alkyl group of the alkylsilyl has a chain length of from 8 to 20 carbon atoms, preferably 8 or 18 carbon atoms and the alkylsilyl is bonded to the silica particles via the silyl group. Suitably, the alkylsilyl-modified silica particles have a particle size in the range of about 1 to 10 μm, preferably, 2 to 5 μm, in particular, 2.5 to 3 μm.

Typically, the mobile phase of the LC column is a polar solvent or mixture of polar solvents. Preferably, the composition of the mobile phase for the LC column may be varied over the time period during which the organic acid compounds are eluted from the LC column. Initially, the polar solvent employed as the mobile phase may comprise a mixture of water and a $C_1$ to $C_3$ alcohol, preferably, methanol. Typically, the ratio of alcohol to water in the polar solvent employed as the mobile phase is initially in the range of 8:1 to 9.5:1. The amount of water in the polar solvent may then be gradually or incrementally reduced until the polar solvent comprises 100% by volume of alcohol i.e., a "gradient programme" is employed. Suitably, a carboxylate salt (preferably, an acetate salt) may be added to the polar solvent as a modifier to enhance separation of the organic acid compounds in the LC column of the LC-MS apparatus. The carboxylate salt is preferably an ammonium salt, for example, ammonium acetate. The concentration of carboxylate salt in the polar solvent may be in the range of from 5 to 15 mM, preferably, 7.5 to 12.5 mM.

Typically, the injection rate for the mobile phase (carrier fluid) is in the range of 0.2 to 0.5 m L/min, for example, about 0.3 mL/min.

Typically, the extracted organic acid compounds (for example, extracted carboxylic acids) have at least one hydrophilic functional group (for example, carboxylate group) and at least one hydrophobic or lipophilic (hydrocarbyl) group. More hydrophobic molecules in the mobile phase (e.g., having a more hydrophobic hydrocarbyl group) will tend to adsorb preferentially to the relatively hydrophobic stationary phase such that more hydrophilic carboxylic acids will tend to elute first from the LC column. Accordingly, the order in which the organic acid compounds are eluted from the LC column will be dependent on their hydrophilic-lipophilic balance (HLB) values.

In addition to the liquid chromatography (LC) column and mass spectrometer (MS), the LC-MS apparatus used in the method of the present invention may include an interface that efficiently transfers the separated organic acid compounds eluted from the LC column into the ionization source of the MS. This interface is necessary when the LC column and MS are incompatible. While the mobile phase in a LC column is a pressurized liquid, the MS analyzers commonly operate under vacuum (around $10^{-6}$ torr). Thus, it is may not be possible to directly pump the eluate from the LC column into the ionization source of the MS. The interface is a mechanically simple part of the LC-MS apparatus that removes a significant portion of the mobile phase used in the LC column and transfers the organic acid compounds to the ionization source of the MS where the compounds are ionized. An interface is not required if the ionization source is of sufficiently high temperature that the mobile phase evaporates before the separated and ionized organic acid compounds reach the analyzer of the MS. Typically, an Orbitrap MS (see below) does not require an interface.

The MS is a high resolution mass spectrometer (HRMS). In HRMS, the resolution may be expressed as (m/$\Delta$m) where $\Delta$m is the width of the peak at a height which is a specified fraction of the maximum peak height. A common standard, well known to the person skilled in the art, is based on $\Delta$m being defined as the Full Width of the peak at Half its Maximum height (FWHM). The high resolution mass spectrometer used in the present invention typically has a resolution of greater than 50,000 FWHM, preferably, greater than 100,000 FWHM at a m/z value of, for example, 400. Suitably, a mass spectrum for the separated organic acid compounds may be obtained using one of the following mass spectrometers (analyzers): Fourier Transform-Ion Cyclotron Resonance-Mass Spectrometers (FT-ICR-MS), Time of Flight-Mass Spectrometers (TOF-MS) and Ion Trap-Mass Spectrometers (IT-MS) such as an orbitrap mass spectrometer.

Preferably, the ionization method used in the MS of the LC-MS apparatus is one that involves ionizing the organic acid compounds, for example, carboxylic acid compounds to generate charged molecules (organic ions) while minimizing fragmentation of these ions.

Suitably the LC-MS apparatus uses atmospheric pressure ionization (API) strategies like Negative Ion Electrospray Ionization (ESI-), or Negative Ion Atmospheric Pressure Photo-ionization (APPI-).

The different ionization methods used will each give a different mass spectrum that is characteristic of the crude oil extract. In one embodiment of the invention, a single ionization technique is used in the liquid chromatography-mass spectral analysis of the sample of the solution of the extracted organic acid compounds, preferably, this single ionization technique is ESI(-).

For ESI(-), the voltage difference at the inlet to the mass spectrometer is set so that the separated organic acid compounds from the LC column of the LC-MS apparatus become ionized when injected into the ionization source but do not substantially fragment. The voltage setting of a HRMS that achieves ionization while minimizing fragmentation is well known to the person skilled in the art.

For APPI(-), ionization is achieved via a different mechanism. Typically, the separated organic acid compounds (molecules) from the LC column of the LC-MS apparatus are irradiated with UV radiation resulting in excitation of the molecules with loss of electrons from the molecules resulting in the formation of radical cations. The ions may also be generated indirectly through excitation of a dopant, for example, toluene, that may be added to the solution of the extracted acids.

Typically, the MS (e.g., Orbitrap MS) records m/z data for the organic acid compounds as they are eluted from the LC column and are ionized in the MS. The HRMS measures the mass-to-charge ratio (m/z) of organic ions very precisely which makes it possible to assign unique elemental compositions to the peaks associated with each m/z value. Thus, the peaks in the extracted ion chromatogram for the crude oil extract are assigned to specific ionized organic acid compounds. The areas under the peaks of the extracted ion chromatogram assigned to one or more specific ionized organic acid compounds may then be determined.

The area under a peak in the extracted ion chromatogram for the crude oil extract assigned to a specific organic acid compound may be compared with an area under a peak in an extracted ion chromatogram obtained for a sample comprising a specific volume of a standard solution of one or more standard organic acid compounds. Such standard solutions are often referred to in the art as "external standards". The standard solution may comprise known concentration(s) of the standard organic acid compound(s) in a polar solvent, typically, a $C_1$ to $C_3$ alcohol, in particular, methanol. The standard organic acid compound may be a carboxylic acid, for example, a $C_{10}$ to $C_{20}$ fatty acid (alkanoic acid), in particular, dodecanoic acid, hexadecanoic acid or octadecanoic acid having DBE values of 1 or a cyclohexyl alkanoic acid or cyclopentyl alkanoic acid having DBE values of 2, in particular, cyclohexyl pentanoic acid. Standard carboxylic acids with higher DBE values may also be used if the peak is assigned to a specific organic acid compound(s) having a higher DBE value than 2.

Preferably, data for these standard solutions are obtained using the same LC-MS apparatus used to analyse the sample of the solution of the extracted organic acid compounds.

Preferably, extracted ion chromatograms are obtained for specific volumes of a plurality of standard solutions having different precisely known concentrations of at least one standard organic acid compound. Calibration curves may be obtained that plot the relative abundance of the peaks assigned to the standard organic acid compounds in the extracted ion chromatograms against the known concentrations of the standard organic acid compound in the standard solutions. Typically, these calibration curves are linear. Linear regression analysis may be used to obtain an equation that correlates the areas under the peaks in the extracted ion chromatograms (assigned to the standard organic acid compound) with the concentrations of the standard organic acid compound in the standard solutions. Different equations may be obtained for different standard organic acid compounds.

It is envisaged that each standard solution may comprise a precisely known concentration of a single standard organic acid compound or precisely known concentrations of a plurality of standard organic acid compounds. Where the standard solutions comprise a plurality of standard organic acid compounds, the concentrations of each standard organic acid compound may vary independently. Equations may be obtained (as described above) that correlate the areas under the peak(s) in the extracted ion chromatograms assigned to the standard organic acid compound(s) with the concentrations of the standard organic acid compound(s).

Typically, the concentrations of the standard organic acid compound(s) in the standard solutions are chosen so as to span a concentration range of from 0.01 to 10 ppm (mg/L). One or more of the equations together with the area under the peak assigned to the specific organic acid compound (in the extracted ion chromatogram obtained for the sample of the solution of the extracted organic acid compounds) may be used to determine the concentration of the specific organic acid compound in the sample of extract.

Typically, the standard organic acid compound(s) (i.e., an acid of known chemical composition) is selected so as to have a similar composition to the individual organic acid(s) assigned to the peak(s) in the extracted ion chromatogram obtained for the sample of the solution of the extracted organic acid compounds. For example, if the peak in the extracted ion chromatogram, obtained for the sample of the solution of the extracted organic acid compounds is assigned to a saturated unbranched (straight chain) fatty acid, a straight chain fatty acid may be used as the standard organic acid compound. If the peak in the mass spectrum is assigned to a monocyclic naphthenic acid, a cyclopentylalkanoic acid or cyclohexylalkanoic acid may be used as the standard organic acid compound.

It is also envisaged that a standard organic acid compound may be added to the solution of the extracted organic acid compounds in a known amount (referred to in the art as an "internal standard"). In this case, the peak for the internal standard should not interfere (overlap) with the peaks for the organic acid compounds derived from the extract.

The method of the present invention may be used to determine the amounts of one or more of the specific (individual) organic acid compounds in the extract.

The method of the present invention may also be used to determine the amounts of one or more classes or series of homologous organic acid compounds in the extract. Thus, the method of the present invention may be used to determine the amounts of the organic acid compounds assigned to peaks in the extracted ion chromatogram for the class or series of homologous organic acid compounds. The total amount (concentration) of the organic acid compounds in the class or series of homologous organic acid compounds may be obtained by summing the values obtained for the amounts (concentrations) of the specific organic acid compounds in the class or series of homologous organic acid compounds, for example, using a calibration curve. It is also envisaged that the areas under the peaks assigned to a class or series of homologous organic acid compounds may be summed and the summed area may then be used to obtain the amount (concentration) of the organic acid compounds in the class or series of homologous organic acid compounds, for example, using a calibration curve.

Preferably, the series or class of homologous organic acid compounds is a class or series of carboxylic acid compounds having a specific DBE value, in particular, DBE values of 1 or 2 (or DBE values of both 1 and 2). It has been found that the class or series of homologous carboxylic acid compounds having a DBE value of 1 may change in concentration between different samples of crude oil, for example, by at least ±2.5%, in particular, at least ±5%. It has also been found that the class or series of homologous carboxylic acid compounds having a DBE value of 2 may remain substantially unchanged in concentration between different samples of crude oil, for example, may have changes in concentration of less than ±1.0%, in particular, less than ±0.50%.

The class of homologous carboxylic acid compounds may be selected from:

1. The class of homologous compounds of general formula $C_xH_yO_n$ wherein x is an integer in the range of 5 to 100 preferably 8 to 75, more preferably 8 to 60, in particular 10 to 45, y is an integer $\leq 2x+2$, and n is an integer in the range of 1 to 10, preferably, 1 to 5, more preferably, 1 to 3, in particular, 2.

2. The class of homologous compounds of general formula $C_xH_yO_n$ (having DBE values of from 1 to 5) wherein x, y and n are as defined above, 3. The class of homologous compounds of general formula $C_xH_yO_n$ (DBE=1, 2 or both) wherein x, y and n are as defined above, 4. The class of homologous compounds of general formula $C_xH_yO_2$ (DBE=1, 2 or both) wherein x, and y are as defined above, The person skilled in the art will understand that DBE is a way of expressing the degree of unsaturation of an organic compound. Assignment of DBE values to each of the formulae assigned from the m/z numerical values of a mass spectrum is a long established analytical technique. A DBE of 1 corresponds to either one π bond (C=C bond or C=O bond) or one closed fully saturated ring. It can be seen that saturated aliphatic monocarboxylic acids have a DBE of 1; monocyclic naphthenic acids having a single carboxylate functional group and no sites of ethylenic unsaturation have a DBE of 2; benzoic acid and phenyl acetic acid have a DBE of 5.

The person skilled in the art will understand that the members of a class of homologous compounds have the same general formula but may differ in their structure. The person skilled in the art would also understand that a homologous series within a class of homologous compounds refers to a group of compounds that differ only by the number of $CH_2$ units in their main carbon chain (for branched carbon chains) or in their single carbon chain (for unbranched carbon chains). The person skilled in the art will also understand that there are many different classes of homologous organic acid compounds in crude oil.

Optionally, a recovery factor acid (i.e., an organic acid) may be added to the sample of crude oil at a known concentration. Suitably, the recovery factor acid is added to the sample of crude oil as a dilute solution in an organic solvent (hereinafter referred to as "standard solution of recovery factor acid"). The standard solution of recovery factor acid may have a concentration of the recovery factor acid of from 0.5 to 5 mg/L, preferably, 0.5 to 2 mg/L, in particular about 1 mg/L. Typically, the amount of the standard solution of recovery factor acid added to the crude oil sample is in the range of 2.5 to 10 µL, preferably, 2.5 to 0.75 µL, for example, 5 µL.

An example of a suitable recovery factor acid is 1-adamantane carboxylic acid. 1-adamantane carboxylic acid comprises four connected cyclohexane rings and therefore has a high DBE number (see below).

At least a portion of the recovery factor acid is recovered in the extract derived from the sample of crude oil. Accordingly, the extracted ion chromatograms for the solutions of the extracted organic acid compounds in the polar organic solvent(s) will have an extracted peak assigned to the recovery factor acid.

The recovery factor (RF) is preferably determined by taking the same amount of the standard solution of the recovery factor acid (as added to the crude oil sample) and diluting this solution with the same polar organic solvent(s) as used for forming the solution of the extract comprised of the extracted organic acid compounds in the polar organic solvent(s). The resulting solution of the recovery factor acid in the polar organic solvent(s) preferably has the same volume as the solution of the extract in the polar organic solvent(s). The solution of the recovery factor acid is then analysed by liquid chromatography-mass spectrometry in an identical manner to a solution of the extracted organic acid compounds.

The areas under the peak (assigned to the recovery factor acid) in the extracted ion chromatograms obtained for each of the solutions of the extracted organic acid compounds is then compared with the area under the peak (assigned to the recovery factor acid) in the extracted ion chromatogram obtained for the solution of the recovery factor acid. The recovery factor (RF) may be defined as a ratio of the area under the extracted peak (assigned to the recovery factor acid) in the extracted ion chromatogram for the solution of the extracted organic acid compounds and the area under the peak (assigned to the recovery factor acid) in the extracted ion chromatogram for the solution of the recovery factor acid. Alternatively, the recovery factor (RF) may be defined as the area under the peak (assigned to the recovery factor acid) in the extracted ion chromatogram for the solution of the extracted organic acid compounds as a percentage of the area under the peak (assigned to the recovery factor acid) in the extracted ion chromatogram for the solution of the recovery factor acid.

The amounts determined for each of the specific organic acid compounds (or for a class or series of organic acid compounds) in the extract may then be scaled using the recovery factor to provide an amount for the specific organic acid compound or for the class or series of organic acid compounds in the sample of crude oil.

The samples of crude oil may be analyzed at a production facility or may be analyzed in a laboratory remote from the production facility. In order to mitigate the risk of any changes to the chemical composition of the samples, the samples may be refrigerated prior to analysis (for example, may be cooled to a temperature of less than 10° C., in particular, a temperature in the range of 3 to 5° C.). The risk of any changes in the chemical composition of the samples may be further mitigated by ensuring that oxygen is excluded from the samples. In particular, the samples may be stored under an inert atmosphere, for example, under an atmosphere of nitrogen. Preferably, the samples of produced oil are stored for less than 1 month, more preferably, less than 2 weeks, in particular, less than 1 week before analysis.

The present invention will now be illustrated by reference to the following Examples.

EXPERIMENTAL

The crude oils that were analysed using the method of the present invention have the TAN values shown in Table 1.

TABLE 1

TAN Values and Weights of Crude Oil Samples

| Crude Oil | Total Acid Number (mg/g KOH) | Weight of Crude Oil Sample (g) |
|---|---|---|
| 1 | 1.8 | 0.500 |
| 2 | 0.34 | 1.000 |
| 3 | 1.05 | 0.500 |

Materials

A 1 mg/mL solution of 1-adamantane carboxylic acid (recovery factor acid) in dichloromethane (DCM) was prepared.

A mixture of diethyl ether and formic acid (2% by volume of formic acid) was prepared for use as an eluent for a solid phase extraction (SPE) column.

Samples of crude oil were added to sample vials (one sample vial for each crude oil sample) in the amounts specified in Table 1. Each crude oil sample was then diluted with 3 mL of hexane, optionally, followed by addition of 5 μL of the 1 mg/mL solution of 1-adamantine carboxylic acid.

Extraction Procedure

Solid phase extraction (SPE) cartridges (Mega BE-NH2, 1 g, 6 mL), one for each crude oil sample, were arranged vertically in a vacuum filtration rig. Each of the cartridges were labelled.

The vacuum filtration rig comprised a vacuum pump for drawing fluid through the cartridges. A 25 mL glass collection vial was placed under each cartridge for collecting the effluent removed from each cartridge.

The vacuum pump of the filtration rig was turned on to achieve a pressure of about 2 inches of mercury (50.8 torr).

The cartridges were then conditioned with 20 to 30 mL of hexane solvent until the level of the hexane reached the top of the sorbent beds.

The vacuum pump was turned off and the hexane effluent was discarded from each of the collection vials.

The glass vials were replaced under the cartridges and the vacuum pump was turned on.

The diluted samples of crude oil were then transferred to the top of the cartridges. Each sample vial was then washed with a small quantity of hexane (0.25 to 1 mL) and the hexane together with traces of crude oil dissolved therein was then transferred to the top of the SPE cartridges and the solvent was eluted from the sorbent bed of each cartridge.

Each cartridge was then eluted with 20 to 25 mL of dichloromethane (DCM) until the level of the DCM reached the top of the sorbent bed.

The vacuum pump was turned off and the DCM effluent was discarded from the collection vials.

The 25 mL glass vials were replaced under the cartridges and the vacuum pump was turned on.

The cartridges were eluted with 10 mL of diethyl ether (until the solvent level reached the top of the sorbent beds).

The vacuum pump was turned off and the diethyl ether effluent was discarded from the collection vials.

Fresh 25 mL glass collection vials were then labelled, weighed and placed under the cartridges.

The vacuum pump was turned on and each cartridge was eluted with 10 mL of the mixture of diethyl ether and formic acid (until the level of the solvent mixture reached the top of the cartridges).

The vacuum pump was turned off.

The vials (each containing a solution of eluted acids in the mixture of diethyl ether and formic acid) were then removed from the vacuum filtration rig.

The solvent (mixture of diethyl ether and formic acid eluent) was then removed by evaporation using a bead bath (or water) bath leaving behind an extract comprising extracted organic acid compounds.

Following evaporation of the solvent, each vial was reweighed and the mass of the extracted organic acid compounds was determined i.e., mass of acids=(mass of collection vial+extracted acids)−mass of empty collection vial.

Caps were then placed on the collection vials and the extracts comprising the organic acid compounds were kept for liquid chromatography-mass spectrometry analysis.

Preparation of Standard Solutions of Standard Carboxylic Acids for Analysis by Liquid Chromatography-Mass Spectrometry Standard carboxylic acids were used to obtain calibration curves for quantifying the amount of organic acid compounds extracted from each sample of crude oil.

Four stock solutions were prepared comprising solutions of a standard carboxylic acid (1 mg/L) in methanol. These stock solutions were solutions of: (a) dodecanoic acid (C12 fatty acid), (b) hexadecanoic acid (C16 fatty acid), (c) octadecanoic acid (C18 fatty acid) and (d) cyclohexyl pentanoic acid. The weight of the standard carboxylic acid and the weight of methanol for each stock solution was accurately recorded thereby allowing the concentration of the standard carboxylic acid in each stock solution to be accurately determined. The stock solutions were then mixed in different volumetric amounts and with different volumetric amounts of methanol and DCM to obtain a number of standard solutions (containing each of the standard carboxylic acids) for analysis by liquid chromatography-mass spectrometry.

The amount of each stock solution and the amounts of methanol and DCM used to prepare the standard solutions are given in Table 2 below:

TABLE 2

Standard Solutions

| Concentration of fatty acids (ppm) | Amount of each stock solution (µL) | Methanol (µL) | DCM (µL) |
|---|---|---|---|
| 0.1 | 0.1 | 666.6 | 333 |
| 0.5 | 0.5 | 665.0 | 333 |
| 1.0 | 1.0 | 663.0 | 333 |
| 3.0 | 3.0 | 655.0 | 333 |
| 5.0 | 5.0 | 647.0 | 333 |
| 7.0 | 7.0 | 639.0 | 333 |
| 10.0 | 10.0 | 627.0 | 333 |

Preparation of Samples of Solutions of Extracted Acids for Analysis by Liquid Chromatography-Mass Spectrometry A 1000 µL pipette was used to add 1 mL of DCM to each collection vial containing an extract comprised of the extracted organic acid compounds. A 100 µL pipette was used to remove a 50 µL portion of the resulting DCM solution of the extracted organic acid compounds and this portion of the solution was added to a 2 mL glass vial provided with an insert. A 100 µL pipette was then used to add 100 µL of methanol (MeOH) to the glass vial to form a solution of the extracted organic acid compounds in a mixture of DCM and methanol. The glass vial was then capped and the solution mixed, e.g., by shaking.

Preparation of the Optional Recovery Factor Acid Control Sample for Analysis by Liquid Chromatography-Mass Spectrometry 5 µL of the 1 mg/mL solution of 1-adamantane carboxylic acid (recovery factor acid) in dichloromethane was added to an empty labelled glass vial and was made up to a volume of 1 mL with a mixture of DCM and methanol with the resulting solution having a 333:667 volumetric ratio of DCM:methanol. The vial was then capped and the sample was mixed, e.g. by shaking.

Liquid Chromatography (LC) Conditions

The LC-MS apparatus comprised a Liquid Chromatography (LC) column having dimensions of 2.1 mm×100 mm and having a stationary phase of octylsilyl-modified silica particles (C8) with a particle size of 2.7 µm. The following mobile phases were used for the LC column:

Mobile phase A: $H_2O$:MeOH 9:1 by volume+10 mM ammonium acetate; and

Mobile phase B: MeOH+10 mM ammonium acetate.

The LC column was set up with the eluent passing directly into the ESI source of the mass spectrometry (MS) system. Eluent starting conditions were then selected (Mobile phase B: 80% by volume; Mobile Phase A: 20% by volume; 0.3 mL/min.). The amount of Mobile Phase A was then decreased to zero over a period of 2 minutes so that the mobile phase was subsequently 100% Mobile Phase B.

With the pump of the LC system switched on, the samples of extracted organic acid compounds, the samples of the standard carboxylic acid solutions, and the samples of the recovery factor acid solution were injected into the column of the LC system in a predetermined sequence using an injection volume of 5 µL. The standard carboxylic acids were injected in the order of increasing carboxylic acid concentration. Preferably, samples were analyzed in triplicate.

Data Processing—Standard Carboxylic Acids

The concentrations of the standard carboxylic acids (C12, C16 and C18 fatty acids and cyclohexyl pentanoic acid) in each standard solution were calculated.

The relative abundance of peaks assigned to the four standard carboxylic acids in the extracted ion chromatograms for each standard solution were then determined.

Calibration curves were obtained that plotted the relative abundance of the peaks assigned to the standard carboxylic acids in the extracted ion chromatograms recorded for the standard solutions against the known concentrations (in ppm) for the carboxylic acids in the standard solution. Four calibration curves were plotted (one for each standard carboxylic acid standard), each showing a linear relationship. Lines of best fit were determined for each carboxylic acid standard having $R^2$ (coefficient of determination) values of at least 0.99. Equations were then calculated for the lines of best fit for each calibration curve.

Data Processing—Samples of Extracted Organic Acid Compounds

The relative abundance of peaks assigned to the class of carboxylic acids having DBE values of 1 (for an m/z range of from 0 to 800) in the extracted ion chromatograms for each sample of a solution of the extracted acids were determined. Each sample of a solution of the extracted acids was analysed by liquid chromatography-mass spectrometry in triplicate with good reproducibility.

Data Processing—Recovery Factor Acid

Optionally, the relative abundance of the peak assigned to the recovery factor acid (1-adamantane carboxylic acid) in the extracted ion chromatograms obtained for each sample of a solution of the extracted acids (that contain the optional recovery factor acid) may be determined (in triplicate).

The relative abundance of the peak assigned to the recovery factor acid (1-adamantane carboxylic acid) for a recovery factor acid control sample (prepared as described above) may also be determined (in triplicate). This provides an estimate for the amount of organic acid compounds extracted from each sample of crude oil because for 100% extraction of organic acid compounds from the samples of crude oil the relative abundance of 1-adamantane carboxylic acid in the extracted ion chromatograms obtained for the samples of extract and for the control sample should be the same.

Results

Three different samples of Crude Oil (Crude Oils 1, 2 and 3) having the TAN values shown in Table 1 (in the absence of the optional recovery factor acid) were subjected to extraction to obtain three different extracts (Extracts 1, 2 and 3). These extracts were prepared for analysis by liquid chromatography-mass spectrometry, as described above and each extract was analyzed in triplicate thereby generating nine data sets. The amount (weight) of C11-43 carboxylic acid compounds with a DBE of 1 in each sample of the solution of the extracted acids was determined from the area under the peaks for these acids in the extracted ion chromatograms and using the calibration curve for the C18 fatty acid standard. It was then possible to extrapolate to the % weight of these compounds in the entire acid extract and to the % weight of these compounds in the sample of crude oil. The results are presented in Table 3.

| | Weight of Extract (mg) | % Total Crude Oil (by weight) | Weight of C11-C43 compounds of DBE = 1 (μg) | % C11-C43 compounds of DBE = 1 in Acid Extract (by weight) | % C11-C43 compounds of DBE = 1 in Crude Oil (by weight) |
|---|---|---|---|---|---|
| Extract 1_1 | 1.8 | 0.18% | 75.49 | 4.19 | 0.0076 |
| Extract 1_2 | | | 76.71 | 4.26 | 0.0077 |
| Extract 1_3 | | | 72.52 | 4.03 | 0.0073 |
| Extract 2_1 | 1.8 | 0.18% | 75.20 | 4.18 | 0.0073 |
| Extract 2_2 | | | 78.24 | 4.35 | 0.0076 |
| Extract 2_3 | | | 79.19 | 4.40 | 0.0077 |
| Extract 3_1 | 1.4 | 0.14% | 77.65 | 5.55 | 0.0078 |
| Extract 3_2 | | | 78.77 | 5.63 | 0.0079 |
| Extract 3_3 | | | 76.21 | 5.44 | 0.0076 |

The invention claimed is:

1. A method for analyzing a crude oil to determine the amount of at least one organic acid compound contained in the crude oil, the method comprising:
   extracting the at least one organic acid compound from a sample of a known amount of the crude oil to form an extract comprising the at least one organic acid compound and determining the amount of the at least one extracted organic acid compound;
   dissolving the extract in a specific volume of at least one polar solvent to form a solution of the extracted at least one organic acid compound in the at least one polar solvent;
   introducing a sample comprising a specific volume of the solution of the at least one extracted organic acid compound in the at least one polar solvent to an apparatus comprising a reversed phase liquid chromatography (LC) column and a mass spectrometer (MS) arranged in series (hereinafter "LC-MS apparatus") wherein the reversed phase LC column contains a hydrophobic sorbent and a mobile phase for the LC column comprises a polar organic solvent;
   separating the at least one organic acid compound the LC column of the LC-MS apparatus and continuously passing the at least one separated organic acid compound from the LC column to the MS of the LC-MS apparatus to ionize the at least one organic acid compound and to obtain a chromatogram with mass spectral data over time for the at least one ionized organic acid compound;
   determining the area under a peak(s) in an extracted ion chromatogram derived from the mass spectral data assigned to the at least one organic acid compound;
   determining the amount of the at least one organic acid compound in the sample of the solution of the at least one extracted organic acid compound by comparing the area under the peak(s) assigned to the at least one organic acid compound in the extracted ion chromatogram with the area under a peak in an extracted ion chromatogram assigned to a specific amount of a standard organic acid compound; and
   extrapolating from the amount of the at least one organic acid compound in the sample of the solution of the at least one extracted organic acid compound to provide the total amount of the at least one organic acid compound in the extract.

2. The method of claim 1, wherein the at least one organic acid compound is extracted from the sample of a known amount of the crude oil by:
   diluting the sample comprised of a known amount of the crude oil with an organic solvent;
   (ii) passing the diluted crude oil sample through an adsorbent column or cartridge comprising a solid phase sorbent to adsorb at least one organic acid compound from the diluted crude oil sample;
   (iii) passing an eluent comprising at least one volatile polar organic solvent having a boiling point lower than the boiling points of the at least one organic acid compound through the column or cartridge to elute the at least one adsorbed organic acid compound from the sorbent and removing from the column or cartridge an effluent comprising precursor solution of the at least one organic acid compound in the at least one volatile polar organic solvent; and
   (iv) separating an extract comprising the at least one organic acid compound from the eluent by evaporation of the at least one volatile polar organic solvent and determining the amount of the extract.

3. The method of claim 2, wherein the at least one organic acid compound are extracted from the diluted crude oil sample using solid phase extraction (SPE) by passing the diluted crude oil sample through a column or cartridge containing a weakly basic solid phase sorbent that selectively adsorbs the organic acid compounds from the diluted crude oil sample.

4. The method of claim 3, wherein the eluent comprising a major portion of a volatile first polar organic solvent selected from a $C_1$ to $C_3$ alcohol and diethyl ether and a minor portion of a volatile second polar organic solvent selected from a $C_1$ to $C_3$ carboxylic acid solvent is passed through the SPE column or cartridge; a precursor solution comprising the at least one organic acid compound and the eluent is removed from the column or cartridge; and, the eluent is removed from the precursor solution, by evaporation, to give an extract comprising the organic acid compounds.

5. The method of claim 1, wherein the sample of crude oil is diluted with an organic solvent selected from aliphatic organic solvents, aromatic organic solvents, tetrahydrofuran, diethyl ether and halogenated aliphatic organic solvents in a volumetric ratio of organic solvent to the crude oil in the range of 1:1 to 10:1.

6. The method of claim 1, wherein the extract comprising the at least one organic acid compound is dissolved in a specific volume of a mixture of at least one polar organic solvent comprising a halogenated organic solvent and an alcohol solvent to provide the solution of the at least one extracted organic acid compound in at least one one polar organic solvent comprising a mixture of polar solvents.

7. The method of claim 1, wherein a mobile phase comprising at least one polar solvent is passed through the LC column of the LC-MS apparatus at a flow rate of from 0.2 to 0.5 mL/min.

8. The method of claim 1, wherein the LC column has a stationary phase comprised of alkylsilyl-modified silica particles wherein the alkylsilyl is bonded to the silica particles via the silyl group and the alkyl group of the alkylsilyl has a chain length of from 8 to 20 carbon atoms and wherein the alkylsilyl-modified silica particles have a particle size in the range of about 1 to 10 μm.

9. The method of claim 1, wherein the MS has an ionisation source selected from an Atmospheric Pressure Ionization (API) source, a Negative Ion Electrospray Ionization (ESI−) source, or a Negative Ion Atmospheric Pressure Photo-Ionization (APPI−) source.

10. The method of claim 1, wherein the MS of the LC-MS apparatus records m/z data (wherein m is mass and z is charge) for the at least one organic acid compound as as they are eluted from the LC column and are ionized in a MS source.

11. The method of claim 1, wherein the amount of the at one organic acid compound or the amount of a class of homologous organic acid compounds in the sample of the solution of the at least one extracted organic acid is determined using a calibration curve that that plots the areas under the peaks in extracted ion chromatograms obtained for a plurality of standard solutions of at least one standard carboxylic acid against the amounts of the at least one standard carboxylic acid in the plurality of standard solutions.

12. The method of claim 11, wherein the class of homologous organic acid compounds is selected from:
  (a) the class of homologous compounds of general formula $C_xH_yO_n$ having a double bond equivalent (DBE) value of 1, 2 or both, wherein x is an integer in the range of 5 to 100, y is an integer $\leq 2x+2$, and n is an integer in the range of 1 to 10; or
  (b) the class of homologous compounds of general formula $C_xH_yO_2$ having a DBE value of 1, 2 or both, wherein x, and y are as defined above.

13. The method of claim 12, wherein the areas under the peaks in the extracted ion chromatogram assigned to a class of organic acid compounds having a DBE value of 1 is determined and is compared with an area under a peak in an extracted ion chromatogram obtained for a specific volume of a standard solution having a known concentration of one or more $C_{10}$ to $C_{20}$ fatty acids having a DBE value of 1; or, the area under the peaks in the extracted ion chromatogram assigned to a class of organic acid compounds having a DBE value of 2 is determined and is compared with an area under a peak in an extracted ion chromatogram obtained for a specific volume of a standard solution having a known concentration of a cycloalkyl alkanoic acid having a DBE value of 2.

14. The method of claim 1, wherein a known volume of a standard solution of an organic recovery factor acid is added to the sample of oil and a recovery factor (RF) for the at least one extracted organic acid compound is determined by comparing the area under the peak assigned to the recovery factor acid in the extracted ion chromatogram for the solution of the at least one organic acid compound with the area under the peak assigned to the recovery factor acid in an extracted ion chromatogram obtained for a standard solution of the recovery factor acid.

15. The method of claim 1, wherein samples of oil are obtained over time from an oil-bearing reservoir that is subjected to an enhanced oil recovery technique to monitor for changes in the amount of at least one organic acid compound or in the amount of at least one class of organic acid compounds in the crude oil samples over time.

16. A method for analyzing a crude oil to determine the amount of at least one organic acid compound contained in the crude oil, the method comprising:
  extracting the at least one organic acid compound from a sample of a known amount of the crude oil by:
    diluting the sample comprised of a known amount of the crude oil with an organic solvent;
    (ii) passing the diluted crude oil sample through an adsorbent column or cartridge comprising a solid phase sorbent to adsorb at least one organic acid compound from the diluted crude oil sample;
    (iii) passing an eluent comprising at least one volatile polar organic solvent having a boiling point lower than the boiling points of the at least one organic acid compound through the column or cartridge to elute the at least one adsorbed organic acid compound from the sorbent and removing from the column or cartridge an effluent comprising a precursor solution of the at least one organic acid compound in the at least one volatile polar organic solvent; and
    (iv) separating an extract comprising the at least one organic acid compound from the eluent by evaporation of the at least one volatile polar organic solvent and determining the amount of the extract;
  dissolving the extract in a specific volume of at least one polar solvent to form a solution of the extracted at least one organic acid compound in the at least one polar solvent;
  introducing a sample comprising a specific volume of the solution of the at least one extracted organic acid compound in the at least one polar solvent to an apparatus comprising a reversed phase liquid chromatography (LC) column and a mass spectrometer (MS) arranged in series (hereinafter "LC-MS apparatus") wherein the reversed phase LC column contains a hydrophobic sorbent and a mobile phase for the LC column comprises a polar organic solvent;
  separating the at least one organic acid compound in the LC column of the LC-MS apparatus and continuously passing the at least one separated organic acid compound from the LC column to the MS of the LC-MS apparatus to ionize the at least one organic acid compound and to obtain a chromatogram with mass spectral data over time for the at least one ionized organic acid compound;
  determining the area under a peak(s) in an extracted ion chromatogram derived from the mass spectral data assigned to the at least one organic acid compound;
  determining the amount of the at least one organic acid compound in the sample of the solution of the at least one extracted organic acid compound by comparing the area under the peak(s) assigned to the at least one organic acid compound in the extracted ion chromatogram with the area under a peak in an extracted ion chromatogram assigned to a specific amount of a standard organic acid compound; and extrapolating from the amount of the at least one organic acid compound in the sample of the solution of the at least one extracted organic acid compound to provide the total amount of the at least one organic acid compound in the extract.

* * * * *